United States Patent [19]

Hrebeniuk

[11] Patent Number: Plant 7,756

[45] Date of Patent: Dec. 24, 1991

[54] DISTINCT VARIETY OF POINSETTIA NAMED H-527 RED

[76] Inventor: Alexander Hrebeniuk, R.D. #1, Box 118, Sugar Run, Pa. 18846

[21] Appl. No.: 339,528

[22] Filed: Apr. 17, 1989

[51] Int. Cl.[5] ..... A01H 5/00
[52] U.S. Cl. ..... Plt./86
[58] Field of Search ..... Plt./86, 86.4

[56] References Cited

U.S. PATENT DOCUMENTS 4,724,276 2/1988 Ecke, Jr. ..... 47/58

*Primary Examiner*—Howard J. Locker
*Attorney, Agent, or Firm*—Webb, Burden, Ziesenheim & Webb

[57] ABSTRACT

A Poinsettia plant named H-527 Red particularly characterized by its bright red bracts, long lasting bloom centers, long lasting keeping qualities, and large bloom size.

1 Drawing Sheet

BACKGROUND OF THE NEW PLANT

The present invention comprises a new and distinct cultivar of *Euphorbia pulcherrima* known by the varietal name H-527 Red. The new cultivar is a radiation induced sport of the variety Dynasty (H518), U.S. Plant Pat. No. 6,150. The bracts of the new variety are a bright red against a green foliage whereas Dynasty is a dark red against a bluish green foliage. The new variety is shorter than Dynasty with better branching after being pinched.

The new cultivar was discovered in May of 1985 in Sugar Run, Pa.; was first asexually reproduced by cuttings shortly thereafter in Sugar Run, Pa. and has been repeatedly asexually reproduced by cuttings at Sugar Run, Pa. Continued observations from the vegetative cuttings have confirmed that the distinguishing features of this new cultivar come true, remain stable and are retained through successive propagations.

The following traits are determined to be basic characteristics of this new cultivar which in combination distinguished this Poinsettia as new and distinct:

1. Eight and one-half week response time under black cloth.
2. Five to seven breaks after pinch.
3. May be grown single stem or pinch.
4. Top leaves are medium green.
5. Mature leaves are medium green.
6. Petioles are dark red.
7. Veins on top and bottom leaves shine; middle vein on leaves light pinkish green.
8. Stem on bottom and top green and brownish red.
9. Bracts are bright red.
10. The center of the bloom is very long lasting.
11. Blooms have three layers of bracts, type flat.
12. 18–20 leaves have been counted on a fully developed pinch plant bloom.
13. The largest bloom size measured on a single stem of a pinch plant have been 12 inches in diameter.
14. Bracts range in size on a pinch plant from 3 cm. wide and 7 cm. long, to 8 cm. wide and 15 cm. long.
15. In normal blooming, the new cultivar shows color in October and is fully in bloom in the beginning of December.
16. Good for growing in the sun belt.

17. Plants ship well.
18. The new cultivar is resistant to fading and is long keeping, lasting through the Christmas season after showing color in October.
19. The plant height reaches 34 cm. to 40 cm. depending on the growing conditions.

DESCRIPTION OF THE DRAWING

The accompanying photographic drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out in Sugar Run, Pa. The plant history was taken on eight and one-half week plants. The color reading were determined under natural daylight at Sugar Run, Pa. Color References are primarily to the R.H.S. Colour Chart of The Royal Horticultural Society of London.

The plant:

*Growth habit.*—Very compact medium growth. After pinching, very freely branching. Branches only in response to pinching.

*Rooting.*—Fast and even.

*Blooming season.*—Eight and one-half weeks. The diameter of the plant can reach 40 cm. to 45 cm. in diameter.

*Blooming habit.—l Medium bracts develop in treble rows; long lasting and can be grown under cool and warm conditions. Responds well under black cloth.*

Foliage:

*Size.*—From 7 cm. wide and 11 cm. long to 9 cm. wide and 13 cm. long.

*Quantity.*—Up to nine leaves per flowering stem; long lasting.

*Color.*—New Foliage — Upper side, Green Group 137 B. Under side, Green Group 137 D. Old foliage — Upper side, Green Group 137 B. Under side, Green Group 137 D. Leaf petiole — Greyed-Purple Group 183 A.

*Shape.*—Oak and heart on pinched plant.

*Texture.*—Upper side is smooth, under side is rough because of veins.

*Edge of margin.*—Varied with the upper leaves approaching lobed, and the lower leaves approaching crenate.

*Disease resistance.*—Resistant to Botrytis.

Flower:

*Borne.*—A small tight corymb.

*Quantity.*—Eight per stem. Can be more or less, by 1-3, depending on growing conditions on a pinched plant. Each one has a nectary.

*Color.*—When mature, the color on Ovaries is Green Group 142 B and Red Group 50 A. The nectar cups are Yellow Group 13 A.

Bracts:

*Size.*—3 cm. wide and 7 cm. long, to 8 cm. wide and 15 cm. long.

*Quantity.*—18 to 20 bracts.

*Color.*—Red Group 52 A.

Reproductive organs: Typical for Poinsettia cultivars.

*Shape.*—Flat, some heart but most oval with long point on ends.

*Margin.*—Wavy.

*Veins.*—Midrib to margin.

I claim:

1. A new and distinct variety of Poinsettia plant as herein shown and described, particularly characterized by its bright red bracts, long lasting bloom centers, long lasting keeping qualities, and large bloom size.

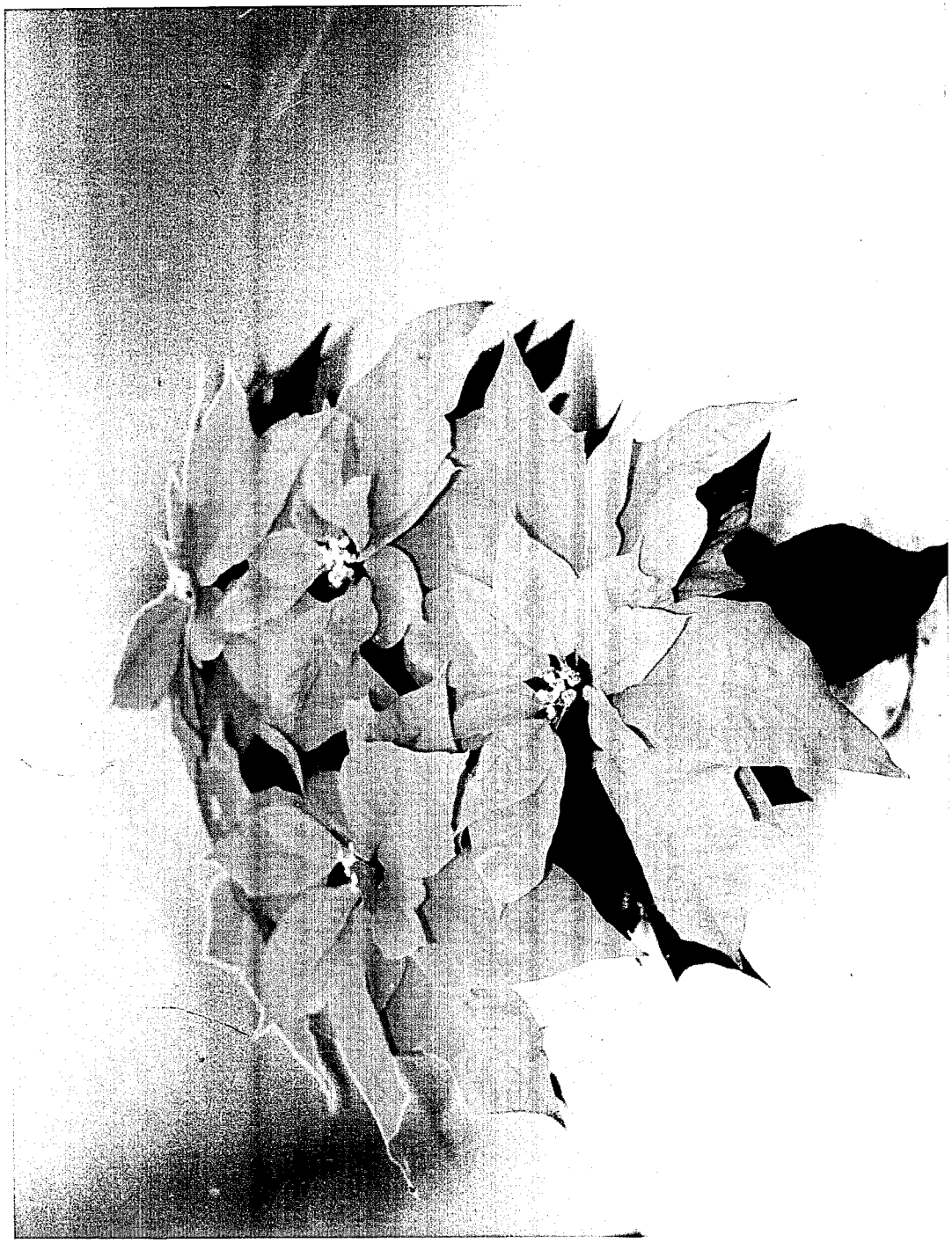

* * * * *